US007871414B2

(12) United States Patent
Hardin, Jr.

(10) Patent No.: US 7,871,414 B2
(45) Date of Patent: Jan. 18, 2011

(54) LOOP TIP WIRE GUIDE WITH OUTER SLEEVE

(75) Inventor: David M. Hardin, Jr., Winston-Salem, NC (US)

(73) Assignee: Wilson-Cook Medical Inc., Winston-Salem, NC (US)

(\*) Notice: Subject to any disclaimer, the term of this patent is extended or adjusted under 35 U.S.C. 154(b) by 319 days.

(21) Appl. No.: 11/966,497

(22) Filed: Dec. 28, 2007

(65) Prior Publication Data

US 2009/0171367 A1 Jul. 2, 2009

(51) Int. Cl.
*A61F 11/00* (2006.01)

(52) U.S. Cl. .................... 606/108; 600/585; 604/93.01; 604/164.01; 604/264; 604/272

(58) Field of Classification Search .................. None
See application file for complete search history.

(56) References Cited

U.S. PATENT DOCUMENTS

| 5,107,852 | A | * | 4/1992 | Davidson et al. ............ 600/585 |
| 5,333,620 | A | * | 8/1994 | Moutafis et al. ............. 600/585 |
| 5,797,856 | A | * | 8/1998 | Frisbie et al. ............... 600/585 |
| 2004/0106878 | A1 | | 6/2004 | Skujins et al. |
| 2004/0167442 | A1 | | 8/2004 | Shireman et al. |
| 2004/0199088 | A1 | * | 10/2004 | Bakos et al. ................. 600/585 |
| 2005/0054952 | A1 | | 3/2005 | Eskuri et al. |
| 2006/0100545 | A1 | * | 5/2006 | Ayala et al. ................. 600/585 |
| 2007/0135734 | A1 | | 6/2007 | Reynolds et al. |

FOREIGN PATENT DOCUMENTS

| EP | 1 346 747 A2 | 9/2003 |
| EP | 1 525 896 A2 | 4/2005 |
| EP | 1 847 289 A2 | 10/2007 |
| WO | WO 2005/014094 A1 | 2/2005 |
| WO | WO 2006/039217 A1 | 4/2006 |

OTHER PUBLICATIONS

PCT International Search Report for PCT/US2008/087112, filed Dec. 17, 2008.
PCT Written Opinion for PCT/US2008/087112, filed Dec. 17, 2008.

\* cited by examiner

*Primary Examiner*—Todd E Manahan
*Assistant Examiner*—Naquan Ishman
(74) *Attorney, Agent, or Firm*—Brinks Hofer Gilson & Lione

(57) ABSTRACT

A wire guide has first and second portions with first and second diameters, respectively. The second portion is located distal of the first portion. A resilient loop positions a distal end of the wire guide adjacent another section of the wire guide. A closure member maintains the distal end in a fixed position relative to the remainder of the wire guide. An outer sleeve may be positioned around one or more parts of the wire guide. A radiopaque element may be secured to the outer sleeve.

23 Claims, 3 Drawing Sheets

LOOP TIP WIRE GUIDE WITH OUTER SLEEVE

FIELD OF THE INVENTION

The present invention relates to wire guides used in the placement of medical devices. More specifically, the present invention relates to a wire guide having a loop tip.

BACKGROUND OF THE INVENTION

Wire guides are elongate flexible members used to provide a path along which another medical device can be moved. The path provided by the wire guide can be used to navigate another medical device, such as a catheter, through a body vessel. The use of wire guides to define such a path is known in the art. Briefly, a wire guide is navigated through a body vessel toward a point of treatment. Once positioned within the vessel, a second medical device, frequently a cannula such as a catheter, is placed over the wire guide and moved along its length toward the point of treatment. Thus, the wire guide provides an established path for placing other devices, eliminating the need for performing delicate navigation procedures for each device passed into the body lumen.

During placement of a wire guide, an operator must navigate the wire guide through the body lumen. Often, the body lumen defines a torturous path due to the presence of natural bends and/or curves, or unnatural impediments, such as tumors, build-ups, and/or strictures. The presence of a torturous path may make navigation of a wire guide difficult. For example, the presence of an impediment may block the wire guide from navigating further into the body lumen. In addition, the presence of a tortuous path may make it difficult to determine the position of the wire guide within the body lumen.

There is an unmet need for a wire guide that can navigate a tortuous path having impediments in which the path and position of the wire guide can be reliably monitored during the navigation.

BRIEF SUMMARY OF THE INVENTION

In a first aspect, a wire guide capable of manipulation about at least one of a tortuous path and an impediment is provided. An elongate member having a first portion and a second portion is provided. The second portion is located distal of the first portion. A loop is provided having an interior space, wherein the loop is affixed to the second portion. An outer sleeve is disposed along at least a portion of the loop.

In a second aspect, a wire guide is capable of manipulation about at least one of a tortuous path and an impediment is provided. An elongate member having a first portion with a first diameter and a second portion with a second diameter smaller than the first diameter is provided. The second portion is located distal of the first portion. A loop having an interior space, wherein the loop is affixed to the second portion, is also provided. A neck portion has a third diameter at a widest point of the neck portion, the third diameter being greater than the second diameter and smaller than the first diameter. The neck portion is positioned between the first portion and the second portion. A first outer sleeve is disposed along a loop and a second outer sleeve is disposed along the neck portion.

In a third aspect, the loop of the wire guide comprises a radiopaque member disposed thereover. The radiopaque member provides the loop tipped wire guide with enhanced radiopacity and/or other properties.

DETAILED DESCRIPTION OF THE INVENTION

Figure 1:
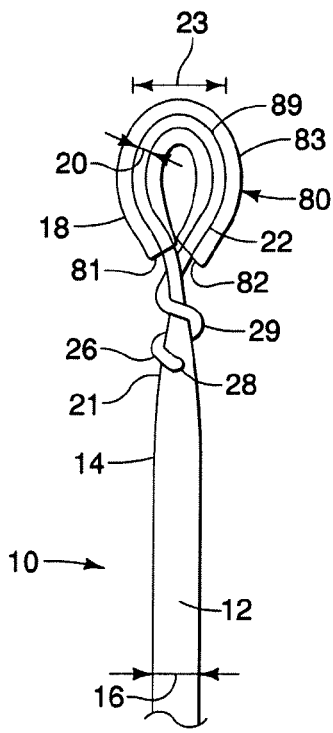
FIG. 1 is a side view of a wire guide according to a first embodiment of the invention in which an outer sleeve is wrapped around the loop portion of the wire guide.

FIG. 1 illustrates a wire guide 10 according to a first embodiment of the present invention. The wire guide comprises an elongate member 12 having a first portion 14 with a first diameter 16 and a second portion 18 with a second diameter 20. The second portion 18 is located distal of the first portion 14. The second diameter 20 is smaller than the first diameter 16. The elongate member 12 has an intermediate portion 21 that defines a taper from the first diameter 16 to the second diameter 20.

The elongate member 12 defines a loop 22 which is closed by closure member 29. In the presently preferred embodiment, the loop 22 comprises a section of the elongate member 12 bent back upon itself. As illustrated in FIG. 1, the second portion 18 preferably defines the entire loop 22. Alternatively, the second portion 18 may define only a portion of the loop 22, and an intermediate portion 21 defines at least a portion of the loop 22. The taper of the intermediate portion 21 provides additional flexibility to the wire guide 10, facilitating navigation of the loop 22 through the torturous path.

Preferably, as illustrated in FIG. 1, the loop 22 comprises a curvilinear loop forming a generally ovoid shape. Also preferably, the loop 22 has a loop width 23 that is greater than the first diameter 16 of the first portion 14 of the elongate member 12. The term 'loop width' as used herein refers to the distance between the two outer most surfaces of the bent sleeve 80 (discussed below) disposed about the elongate member 12 at the widest portion of the loop 22.

The elongate member 12 has a distal end 26 and a distal tip 28. Preferably, the distal tip 28 tapers from the second diameter 20 to a smaller diameter, and preferably tapers to a point. As illustrated in FIG. 1, the loop 22 is preferably formed in a manner that positions the distal end 26 adjacent the intermediate portion 21. Preferably, this placement also positions the distal tip 28 adjacent the intermediate portion 21. Such placements provide a low profile over the portion of the elongate member 12 that has a double width (i.e., two sections of the elongate member 12). Other embodiments are contemplated in which the distal end 26 is positioned adjacent to the first portion 14 or the second portion 18 of the elongate member 12.

Any method of forming the loop 22 is contemplated. In one preferred embodiment, the closure member comprises a coil 29. More specifically, two sections of the elongate member 12 are wound about each other. Preferably, the distal end 26 is wound such that a low profile is achieved.

FIG. 1 shows an outer sleeve 80 slidably disposed along the loop 22. The term "sleeve" as used herein refers to any discrete structure adapted to be disposed about the loop 22, including but not limited to a coiled structure, a cylindrical structure, or a helical structure. The outer sleeve 80 may be sufficiently radiopaque so as to allow a physician or other operator to fluoroscopically observe the loop 22 as it is being navigated through a body lumen. The term "radiopaque" as used herein refers to any type of material or structure that blocks radiation from being transmitted therethrough, thereby making the material or structure visible under x-rays.

Figure 2:
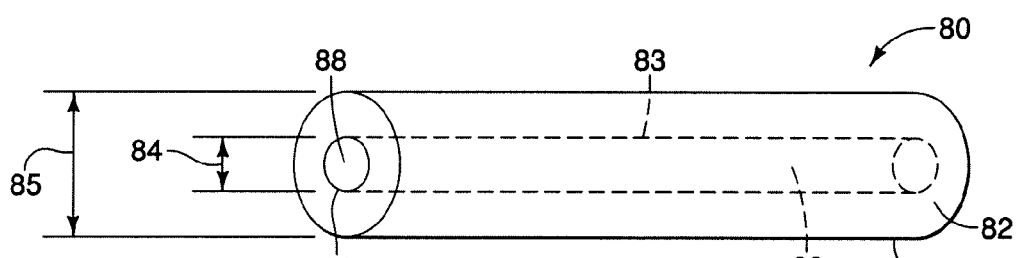
FIG. 2 is a side view of the outer sleeve shown as unbent.

FIG. 2 shows the outer sleeve 80 in an unbent configuration and unattached to the loop 22 of the wire guide 10. The outer sleeve 80 comprises a first end 81, a second end 82, and a body portion 83 extending between the first and second ends 81 and 82. Preferably, the outer sleeve 80 is slidably disposed over the entire loop 22, as shown in FIG. 1, so as to increase the radiopacity of the entire loop 22.

The inner diameter 84 (FIG. 2) of the outer sleeve 80 may be assembled onto the loop 22 as follows. The wire guide 10 is extended linearly out so as to create a single, tapered wire having a first diameter 16 at a first portion 14, a second diameter 20 smaller than the first diameter 16 at a second portion 18, and an intermediate portion 21 between the first diameter 16 and the second diameter 20. The outer sleeve 80 may then be slid over the distal end of the wire guide 10 so as to position the outer sleeve 80 about the second portion 18. With the outer sleeve 80 secured over the second portion 18, the second portion 18 and the outer sleeve 80 are bent to create the loop 22 as shown in FIG. 1. The distal end 26 of the second portion 18 is then wound about the intermediate portion 21. The distal tip 28 of the second portion 18 rests at the intermediate portion 21. The inner diameter 84 of the outer sleeve 80 is less than the first diameter 16 of the first portion 14. As a result, the outer sleeve 80 need not be further secured to the wire guide 10. The first and second ends 81 and 82 of the outer sleeve 80 remain freely movable about the second portion 18. Having the outer sleeve 80 slidably disposed about the second portion 18 maintains the flexibility of the loop 22 as the wire guide 10 encounters impediments along a tortuous body lumen.

Other means for securing the outer sleeve 80 onto the loop 22 are contemplated. For example, the sleeve 80 may be affixed onto the second portion 18 of the loop 22 by the use of adhesives, fusion bonding (i.e., annealing at elevated furnace temperatures as to create a solid bond), or soldering. Such securing means may alter the flexibility and resiliency of the loop 22 as needed. Other means for securing the sleeve 80 may be used as known to one of ordinary skill in the art.

The sleeve 80 may be made from any type of biocompatible material. In one embodiment, the material may be a suitable thermoplastic polymer such as high density polyethylene (HDPE), polytetrafluorethylene (PTFE), polyethylene ethyl ketone (PEEK), polymethylmethacrylate (PMMA), polyimide, Ethylene Tetrafluoroethylene (ETFE), and polyether block amides. For use with guide wires, the polymer layer has a thickness ranging from about 0.001 to about 0.01 inches, and more preferably about 0.002 to about 0.005 inches. Such a thickness allows the loop 22 to retain flexibility.

The outer sleeve 80 may comprise a radiopaque element 89 disposed along the body portion 83 (FIG. 2). The sleeve 80 and radiopaque element 89 may be formed from any number of suitable materials and possess any number of suitable structures. In a preferred embodiment, the outer sleeve 80 is formed from a tungsten coiled structure, and elemental gold is secured onto the outer sleeve 80 by electroplating the elemental gold onto the tungsten coiled structure. The term "secured" as used herein is intended to encompass any means by which a radiopaque element may be bounded to a sleeve, including but not limited to embedding, anchoring, chemically bonding, physically bonding, heat bonding, soldering, welding, impregnating, plating, and dip coating a radiopaque element to a sleeve 80. The electroplating process involves using electrical current to deposit onto the tungsten coil a relatively thin layer of elemental gold. The current density, which is determined by the ratio of the electroplating current and the surface area of the tungsten coil to be plated, may determine the deposition rate of the elemental gold, the electroplating adherence of the elemental gold, as well as the overall quality of the electroplating of the elemental gold. The plating of elemental gold onto the tungsten coil may provide enhanced fluoroscopic imaging.

In another plating process, the entire exterior of the tungsten coiled structure may be plated with the radiopaque material (e.g., elemental gold). Afterwards, the electroplated material is selectively removed from the sleeve 80 by laser ablation, chemical etching, mechanical abrasion or grinding. The thickness of the electroplating material may range from about 0.1 to about 30 microns. Alternatively, the above-described electroplating process may be performed so as to deposit bands of radiopaque material onto the tungsten coiled structure. Selected areas of the tungsten coiled structure are masked so as to prevent electroplating thereon.

Other radiopaque materials such as bismuth, platinum, tin, tantalum, iridium, barium and the like can be secured to the outer sleeve 80. The radiopaque materials may be secured to any surface of the outer sleeve 80.

Securing the radiopaque element 89 to the outer sleeve 80 may be achieved in other ways as well. For example, the radiopaque element 89 may be embedded into the sleeve 80. A mandrel may be used to set the shape of the sleeve 80. After establishing the shape of the sleeve 80, the radiopaque element 89 is applied to the sleeve 80. Alternatively, the radiopaque element 89 may lie over the sleeve 80 and suitable heat shrink material may be applied over the radiopaque element 89 and the sleeve 80.

In yet another embodiment, the radiopaque element 89 may be formed from a shape memory material that is embedded or impregnated into the sleeve 80. For instance, the radiopaque element 89 may be formed from NITINOL, which is a radiopaque nickel-titanium alloy. In one embodiment, the NITINOL may be a cylindrical band that is embedded within the sleeve 80 by utilizing the thermally induced deformation or recovery of the shape memory alloy. Initially, the cylindrical band would have an outer diameter substantially equal to or less than the outer diameter 85 of the sleeve 80. The cylindrical band may then be cooled (e.g., by any conventional cooling method such as liquefied nitrogen) to a sufficiently low temperature below the shape recovering transition temperature so as to cause the shape forming material to become capable of physical deformation to an expanded diameter. While the cylindrical band is at the low temperature, it may be deformed into a deformed, expanded configuration that has a larger diameter than the original configuration. The larger diameter deformed cylindrical band may be obtained by applying a radial outward force to the inner surface of the band by, for example, a shaping rod through the center bore of the band. Once the band has been formed from its original configuration into its deformed configuration as represented by the deformed cylindrical band, the deformed band is positioned concentrically around the outer surface of the sleeve 80.

Prior to raising the temperature of the NITINOL cylindrical band, a supporting mandrel is inserted through the passageway 88 (FIG. 2) of the sleeve 80 so as to extend longitudinally along the band beyond both ends 81 and 82 of the sleeve 80. The temperature of the NITINOL band is then raised above its predetermined transition temperature using, for example, hot air. As the band is raised to a temperature above the shape transition temperature, the band begins to return to its smaller diameter original configuration by moving radially inward into contact with the outer radial surface of the tubular sleeve 80. Continued movement by the band radially inwardly causes the inner surface of the band to press against outer radial surface of the sleeve 80. Simultaneously, the temperature of the band is high enough to soften and melt the sleeve 80 material immediately adjacent to the band, thereby causing the band to sink into the material of the sleeve 80 until it reaches its original configuration. During the thermally induced deformation or shape recovery process into the original configuration, the support rod supports the inner radial surface of the sleeve against the radially inward force of band thereby maintaining the inner diameter 84 of the sleeve 80. The support rod is then removed resulting in the NITINOL marker securely embedded into the material of the sleeve 80.

Embedding the NITINOL band into the sleeve 80 is advantageous in that the cylindrical NITINOL band melts its way into embedded engagement with the sleeve 80 when moving into a physical rigid configuration, thereby not requiring any adhesives or other less dependable securing means for holding the band in place. Additionally, by sizing the band so that the outer diameter of the original configuration is no greater than the outer diameter of the sleeve 80, the NITINOL marker band can be effectively attached to the sleeve 80 without increasing the sleeve's dimensional changes or creating transitions such as ridges on the outer surface of the sleeve 80. Accordingly, a smooth outer radial surface of the sleeve 80 is maintained, thereby allowing easier navigation of the wire guide 10 through the body lumen.

Other means for embedding or impregnating radiopaque material into sleeve 80 include utilizing radiopaque inks, or the use of radiopaque shrink wrap or tubing over the sleeve 80 (e.g., radiopaque urethane). Alternatively, the sleeve 80 may be dipped into a solution of radiopaque polymer or loaded with radiopaque powder such as tungsten. In another embodiment, the inner diameter of a radiopaque element 89 is affixed to the outer diameter 85 of the sleeve 80 by a heat bond. The region of the sleeve 80 where the radiopaque element 89 is to be bonded is heated and slightly stretched down to enable slidably mounting the band onto the stretched down area.

In addition to the above-described structures for radiopaque element 89, the radiopaque element 89 may possess other types of structures. In one embodiment, the radiopaque element 89 may take the form of ribbons, discrete bands, beads, or strips of foils embedded in the sleeve 80 or affixed to a surface of the sleeve 80. The cross sectional shape of the radiopaque element 89 could be a rectangle, square, ovoid, circle, or the like. Alternatively, the radiopaque element 89 may be a cylindrical sleeve or a helical coil, both of which may be used without the sleeve 80.

Prior to securing the sleeve 80 with the radiopaque element 89, an electrically insulative material 99 is preferably disposed over the outer surface of the sleeve 80 comprising the radiopaque element 89. Any electrically insulative material 99 may be utilized as known in the art. In a preferred embodiment, the electrically insulative material 99 comprises ethylene tetrafluoroethylene (ETFE). Preferably, the ETFE is extruded. The ETFE extrudate 99 may be disposed over the sleeve 80 in which the sleeve 80 preferably is a gold plated tungsten coil. The ETFE extrudate 99 serves as an electrical insulator which allows the material to be used with electrosurgical devices. ETFE is a thermoplastic copolymer derived from the polymerization of ethylene and tetrafluroethylene monomers. The resin is abrasion resistant, possesses a relatively high dielectric strength compared to other plastics and has a relatively low coefficient of friction. Because of its high dielectric strength, the ETFE extrudate 99 is a suitable electrical insulator for use in wire guided applications in which an electrical medical device (e.g., cautery catheter) is advanced over the wire guide 10. The ETFE extrudate 99 as an electrical insulator may prevent electrical current from jumping onto the wire guide 10. The ETFE extrudate 99 is preferably extruded over the outer sleeve 80 (e.g., preferably a tungsten coil) having a radiopaque element 89 in the form of elemental plated gold. In preferred embodiments, the thickness of the ETFE extrudate is between approximately 0.001 and 0.010 inches. In particularly preferred embodiments, the thickness of the extrudate is between approximately 0.001 and 0.005 inches. In still more preferred embodiments, the thickness of the extrudate is between approximately 0.001 and 0.002 inches. [David, please confirm. These preferred thicknesses provide suitable ETFE extrudate thicknesses while not adding significantly to the overall thickness of the device. Other fluoropolymers, polyurethanes, and other suitable electrically insulative materials as are known and used in the medical device arts may be utilized.

Figure 3:
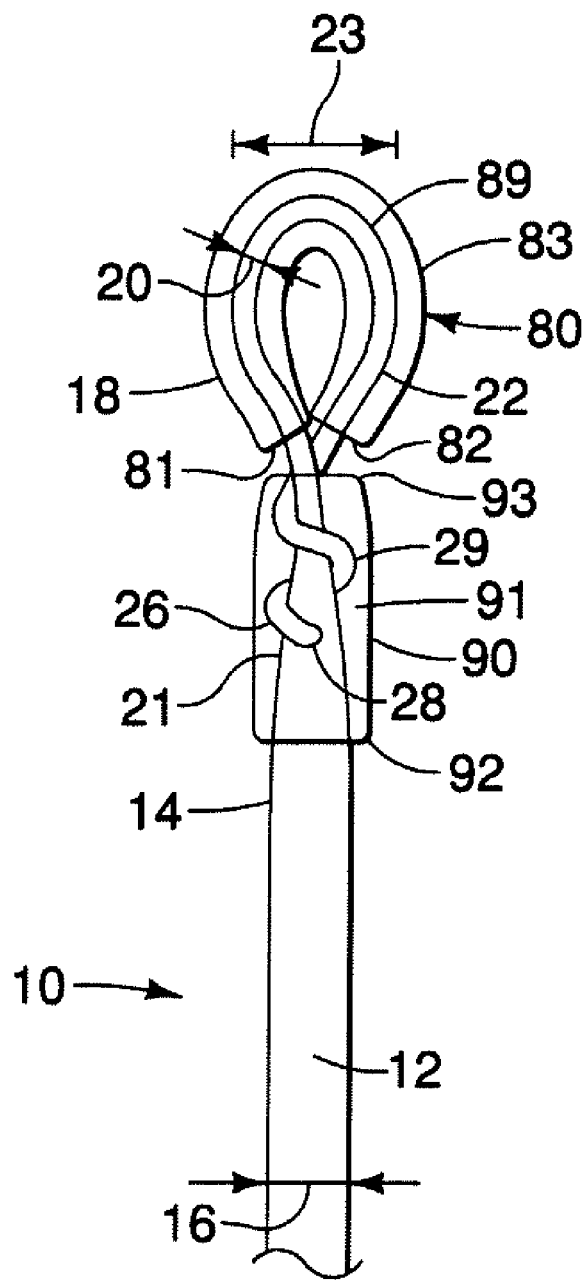
FIG. 3 is a side view of a wire guide according to a second embodiment of the invention in which two outer sleeves are disposed over the distal end of the wire guide.

In another preferred embodiment, the radiopacity may be further enhanced by adding an additional radiopaque structure to the wire guide of FIG. 1. FIG. 3 shows that a second outer sleeve 90 has been added along the neck or intermediate portion 21. The second outer sleeve 90 may comprise a radiopaque element 91. Any radiopaque material may be used for the second outer sleeve 90. Preferably, the second outer sleeve 90 is a platinum coil spring. The platinum coil spring is slidably disposed over the intermediate portion 21. The platinum coil is positioned along the intermediate portion 21 so as to be adjacent to the first outer sleeve 80, which preferably also possesses a radiopaque element 89. The platinum coil has a first end 93 which is in close proximity to sleeve 80. The platinum coil has a second end 92 which preferably extends proximally along the intermediate portion 21. The platinum coil may cover the entire intermediate portion 21, as shown in FIG. 3. Preferably, the platinum coil will have a length ranging from about 3 centimeters to about 5 centimeters.

The platinum coil has an inner diameter 95 which is larger than the outer diameter of the intermediate portion 21 at its widest point and smaller than the outer diameter (i.e., first diameter 16) of the first portion 14. Such a sized platinum coil enables it to remain entrapped along the intermediate portion 21 yet remain slidably disposed along the intermediate portion without reducing the flexibility of the wire guide 10. The platinum coil may be assembled onto the intermediate portion 21 by introducing it from the proximal end of the wire guide 10. The second outer sleeve may be formed from other radiopaque materials known to one of ordinary skill in the art besides platinum. Additionally, the second outer sleeve 90 may comprise various other structures besides a coiled structure.

Figure 6:
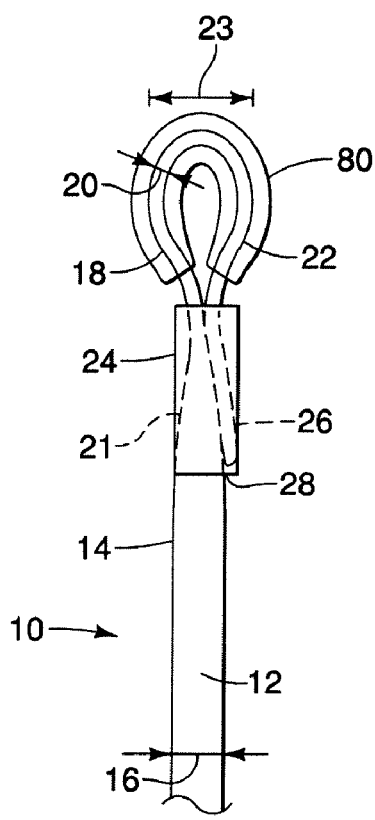
FIGS. 4-6 are variants of a loop tip wire guide which may incorporate a first and a second outer sleeve.
Figure 5:
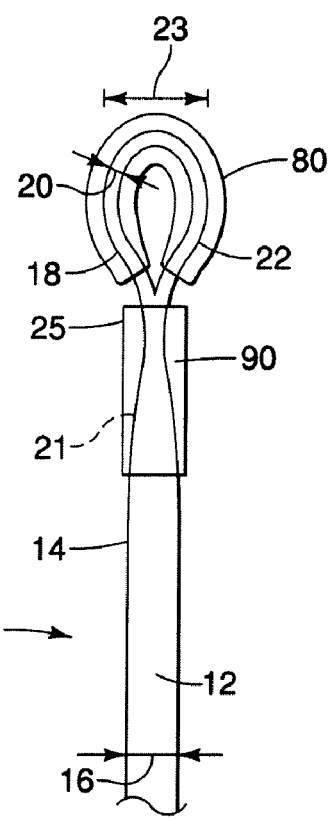
Figure 4:
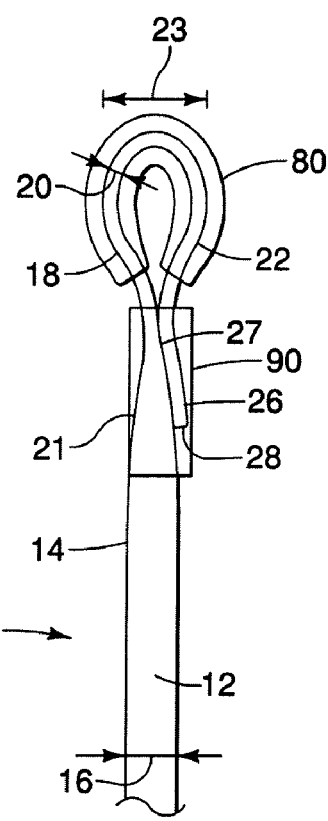

Although sleeves 80 and 90 have been described with reference to the loop tip wire guide of FIG. 1, the radiopaque sleeves 80 and/or 90 may be secured to other variations of a loop tip wire guide. For example, FIGS. 4 and 5 represent other types of loop tip wire guides which may have sleeves 80 and 90 disposed therealong, in which the sleeves 80 and/or 90 may be radiopaque. For example, FIG. 4 shows a loop tip wire guide in which two sections of the elongate member 12 are welded or soldered together to form a loop 22. Additionally, sleeve 80 may be configured about the loop 22 of FIG. 6, which shows the closure member 24 as a cannula closing the loop 22 and fixing the loop 22 in overall size. Sleeves 80 and 90 are shown disposed about the loop tip wire guide of FIG. 5. FIG. 5 shows a closure member having a molded bond 25 in which the loop 22 of the wire guide 10 is formed by molding two sections of the elongate member 12 together.

Any suitable material can be used for the elongate member 12, and a variety of suitable materials are known to those skilled in the art. The material chosen need only be biocompatible and able to be formed into the structures described herein. Examples of suitable materials include stainless steel and NITINOL. The elongate member 12 may comprise a wire, a tubular member or a sheet of material. Further, the elongate member 12 can be formed of a series of layers, or as a coated core structure. For example, in one embodiment, the elongate member 12 comprises a NITINOL core with a ETFE covering.

A variety of shapes and sizes of elongate members and loops can be used, and these can both be optimized based on particular applications. The dimensions of the elongate member 12 and loop 22 will depend upon various factors, including the intended use of the wire guide and the vessels into which the wire guide will be positioned. For a wire guide intended to cannulate the common bile duct, suitable dimensions include a first diameter 16 of between approximately 0.016 inches and approximately 0.038 inches, and preferably comprises a diameter of approximately 0.035 inches. The second diameter 20 of the wire guide preferably has a diameter of between approximately 0.003 inches and approximately 0.010 inches, and preferably comprises a diameter of approximately 0.006 inches. The intermediate portion of this wire guide defines a taper between the first diameter 16 and the second diameter 20. The taper may be smaller or approximately the same size as the second diameter 20. Preferably, the intermediate portion defines a taper from approximately 0.006 inches to approximately 0.016 inches. For this wire guide, the loop is preferably ovoid in shape with a length of between approximately 4 millimeters and approximately 5 millimeters, and a width of between approximately 2 millimeters and approximately 3 millimeters.

Also, the outermost surface of the wire guide 10, may be treated with a hydrophilic coating or hybrid polymer mixture, such as those based on polyvinyl puroladine and cellulose esters in organic solvent solutions. These solutions make the wire guide particularly lubricious when in contact with body fluids, which aids in navigation.

As illustrated in the figures, the loop 22 is preferably formed by the elongate member 12. As an alternative, a separate member defining the loop can be affixed to a substantially straight elongate member to form the wire guide of the present invention. This may be advantageous when it is desirable to form the loop and elongate member of different materials. For example, a nylon or silicon loop could be formed and attached, such as by a closure member, to an elongate member formed of NITINOL. Such an assembly could be associated with the outer sleeves 80 and/or 90 as described above, in which a radiopaque element 80 and 91 are secured to their respective outer sleeves 80, 90 for enhanced radiopacity. Additionally, suitable heat shrink material, such as TEFLON, may be applied over a portion of the loop 22 to create a streamlined low profile.

As can be seen, utilizing outer sleeves 80 and/or 90, which have radiopaque elements, ensures reliable monitoring of the position of the wire guide 10 during navigation within a body lumen to ensure that the wire guide 10 is advanced along the intended path.

While preferred embodiments have been described, it should be understood that the preferred embodiments are intended to be limiting in any way, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A wire guide capable of manipulation about at least one of a tortuous path and an impediment comprising:
    an elongate member having a first portion and a second portion, wherein the second portion is located distal of the first portion;
    a loop defining an interior space, wherein the loop is affixed to the second portion; and
    an outer sleeve movably disposed along at least a portion of the loop,
    wherein the first portion of the elongate member has a first diameter and the loop has a second diameter that is smaller than the first diameter.

2. The wire guide of claim 1, wherein the loop is closed by a closure member.

3. The wire guide of claim 1, wherein the outer sleeve is slidably disposed along the loop.

4. The wire guide of claim 1, wherein the outer sleeve comprises a first end and a second end and a body portion extending between the first end and the second end, the body portion being wound around the loop.

5. The wire guide of claim 1, wherein the outer sleeve comprises a radiopaque element.

6. The wire guide of claim 5, wherein the outer sleeve has an inner diameter, the inner diameter being smaller than the first diameter of the first portion of the elongate member and larger than the second diameter of the loop.

7. The wire guide of claim 5, wherein the outer sleeve is disposed within an electrically insulative material.

8. The wire guide of claim 7, wherein the electrically insulative material is formed from ethylene polytetrafluoroethylene (ETFE).

9. The wire guide of claim 5, further comprising a means for securing the radiopaque element to the outer sleeve.

10. The wire guide of claim 5, wherein the outer sleeve comprises tungsten, further wherein the outer sleeve comprises a coiled structure.

11. The wire guide of claim 10, wherein the outer sleeve is plated with elemental gold.

12. The wire guide of claim 11, wherein the outer sleeve wraps around the entire loop, such that the first end and the second end of the outer sleeve rests against an apex of the loop.

13. The wire guide of claim 5, wherein the radiopaque element comprises radiopaque beads, ribbons, discrete bands, strips of foils, or any combination thereof secured to the outer sleeve.

14. The wire guide of claim 5, wherein the outer sleeve imparts flexibility and resiliency to the loop.

15. The wire guide of claim 1, wherein the second portion of the elongate member is bent back upon itself to form the loop.

16. The wire guide of claim 1, further comprising a second outer sleeve, the second outer sleeve being disposed adjacent to the loop.

17. A wire guide capable of manipulation about at least one of a tortuous path and an impediment comprising:
    an elongate member having a first portion with a first diameter and a second portion with a second diameter, the second diameter being smaller than the first diameter, wherein the second portion is located distal of the first portion;
    a loop having an interior space, wherein the loop is affixed to the second portion;

a neck portion having a third diameter at a widest point of the neck portion, the third diameter being greater than the second diameter and smaller than the first diameter, the neck portion being positioned between the first portion and the second portion;

a first outer sleeve movably disposed along the loop; and a second outer sleeve fixedly disposed along the neck portion.

18. The wire guide of claim 17, wherein an electrically insulative material is disposed about and substantially encloses each of the first and the second outer sleeves, the material being formed from ethylene polytetrafluoroethylene (ETFE).

19. The wire guide of claim 17, wherein the second outer sleeve has a longitudinal length of about 5 centimeters.

20. The wire guide of claim 17, wherein the loop comprises a first degree of radiopacity and the first outer sleeve comprises a second degree of radiopacity greater than the first degree of radiopacity.

21. The wire guide of claim 20, wherein the second degree of radiopacity comprises gold plated on a tungsten coil.

22. The wire guide of claim 20, wherein the second outer sleeve comprises a third degree of radiopacity greater than the first degree of radiopacity.

23. The wire guide of claim 22, wherein the third degree of radiopacity comprises a platinum coil.

* * * * *